(12) United States Patent
Liao et al.

(10) Patent No.: US 11,950,763 B2
(45) Date of Patent: Apr. 9, 2024

(54) SELF-PROPELLED SOFT ROBOT BODY

(71) Applicant: Tsinghua University, Beijing (CN)

(72) Inventors: Hongen Liao, Beijing (CN); Boyu Zhang, Beijing (CN); Hexiang Wang, Beijing (CN); Tiantian Zhang, Beijing (CN)

(73) Assignee: Tsinghua University, Beijing (CN)

( * ) Notice: Subject to any disclaimer, the term of this patent is extended or adjusted under 35 U.S.C. 154(b) by 867 days.

(21) Appl. No.: 16/742,422

(22) Filed: Jan. 14, 2020

(65) Prior Publication Data
US 2020/0221938 A1 Jul. 16, 2020

Related U.S. Application Data

(63) Continuation of application No. PCT/CN2018/114117, filed on Nov. 6, 2018.

(30) Foreign Application Priority Data

May 18, 2018 (CN) .......................... 201810480355.3

(51) Int. Cl.
*A61B 1/00* (2006.01)
*A61B 1/015* (2006.01)

(52) U.S. Cl.
CPC ...... *A61B 1/00156* (2013.01); *A61B 1/00057* (2013.01); *A61B 1/00119* (2013.01); *A61B 1/00133* (2013.01); *A61B 1/015* (2013.01)

(58) Field of Classification Search
CPC ............ A61B 1/00119; A61B 1/00133; A61B 1/00148; A61B 1/00156; A61B 1/015
See application file for complete search history.

(56) References Cited

U.S. PATENT DOCUMENTS 4,176,662 A * 12/1979 Frazer .................. A61B 8/0841
600/114
4,676,228 A * 6/1987 Krasner ............. A61B 1/00082
600/116
(Continued)

FOREIGN PATENT DOCUMENTS

CN 1753762 A 3/2006
CN 101179978 A 5/2008
(Continued)

OTHER PUBLICATIONS

English translation of Fourth Office Action dated Jan. 1, 2021 for CN2018104803553.
(Continued)

*Primary Examiner* — Aaron B Fairchild
(74) *Attorney, Agent, or Firm* — DINSMORE & SHOHL LLP

(57) ABSTRACT

Disclosed is a self-propelled soft robot body, including a tube which is internally and axially provided with a tube cavity, and at least one propelling structure, comprising a first driving unit, a second driving unit and a third driving unit, which are evenly fixed on a peripheral wall of the tube cavity, relative to an axis thereof, and along the axis of the tube; and the first driving unit, the second driving unit and the third driving unit are respectively telescopic along the axis of the tube; at least two support structures, with each two adjacent support structures having at least one propelling structure arranged therebetween, the support structures are fixedly connected with the propelling structure and arranged on the peripheral wall of the tube cavity.

13 Claims, 14 Drawing Sheets

(56) References Cited

U.S. PATENT DOCUMENTS

| | | | | |
|---|---|---|---|---|
| 5,906,591 | A * | 5/1999 | Dario | A61B 17/00234 600/114 |
| 2002/0107478 | A1 * | 8/2002 | Wendlandt | A61B 1/0052 604/95.01 |
| 2004/0073082 | A1 * | 4/2004 | Phee Soo Jay | A61M 25/0116 600/101 |
| 2006/0028041 | A1 | 2/2006 | Ono et al. | |
| 2007/0276181 | A1 * | 11/2007 | Terliuc | A61B 1/00154 600/106 |
| 2009/0314119 | A1 | 12/2009 | Knoll | |

FOREIGN PATENT DOCUMENTS

| CN | 101622107 A | 1/2010 |
|---|---|---|
| CN | 101669809 A | 3/2010 |
| CN | 103006165 A | 4/2013 |
| CN | 104523215 A | 4/2015 |
| CN | 106235993 A | 12/2016 |
| CN | 108652570 A | 10/2018 |
| WO | 2005074377 A2 | 8/2005 |
| WO | 2006090822 A1 | 8/2006 |

OTHER PUBLICATIONS

Written Opinion of International Application No. PCT/CN2018/114117.
First Office Action issued in Chinese Application No. 2018104803553.
Machine Translation for CN101669809A, https://patents.google.com/patent/CN101669809A/en?oq=cn101669809a.
Third Office Action issued in Chinese Application No. 2018104803553.
Second Office Action issued in Chinese Application No. 2018104803553.

* cited by examiner

SELF-PROPELLED SOFT ROBOT BODY

CROSS REFERENCE TO RELATED APPLICATIONS

This disclosure is a continuation of International Application No. PCT/CN2018/114117, filed on Nov. 6, 2018, which is based upon and claims priority to Chinese Patent Application No. 2018104803553, filed on May 18, 2018, the entire contents of which are incorporated herein by reference.

TECHNICAL FIELD

The present disclosure relates to the field of medical device technology, and specifically relates to a self-propelled soft robot body.

BACKGROUND

At present, the insertion part of a medical endoscope is relatively hard compared to human tissues. The endoscope is mainly inserted into the body cavity by push in forcefully from the outside of a patient's body.

The patent document with publication number CN103006165A provides a flexible endoscope robot with variable rigidity, which has a conduit component, a drive component, a fluid supply component and a balloon component. One end of the conduit component is connected to the drive component for propelling the conduit component. The fluid supply component is connected to the balloon component through a fluid tube, and the conduit component is supported in the tract by controlling the degree of expansion of the balloon component. A cord and a rigid fixed joint are embedded into the conduit component, the embedded cord is connected to the first end of the rigid fixed joint, and the second end is connected to the drive component. The drive component controls the pulling of the embedded cord to realize the steering of the conduit component. The flexible endoscope robot realizes the function of changing the propelling direction of the conduit component autonomously according to the bending condition in the tract, so that the rigidity of the device can be changed, and it can move more accurately within the tract, reducing the operation difficulty of the endoscope.

However, the above-mentioned embedded cord and the rigid fixed joint introduce many hidden safety hazards to a surgical process. With improper operation, it will cause very serious scratches, punctures and other injuries to the patient's tract.

SUMMARY

Therefore, the present disclosure is aimed to solve a technical problem of overcoming the deficiency of damages to the tract of a patient in the prior art, thereby providing a self-propelled soft robot body capable of mitigating damages to the tract.

The present disclosure provides a self-propelled soft robot body, including a tube which is internally and axially provided with a tube cavity, and at least one propelling structure, comprising a first driving unit, a second driving unit and a third driving unit, which are evenly fixed on a peripheral wall of the tube cavity, relative to an axis thereof, and along the axis of the tube; and the first driving unit, the second driving unit and the third driving unit are respectively telescopic along the axis of the tube; at least two support structures, with each two adjacent support structures having at least one propelling structure arranged therebetween, the support structures are fixedly connected with the propelling structure and arranged on the peripheral wall of the tube cavity, for fixing at least one end of the self-propelled soft robot body on the tract, and providing support for the self-propelled soft robot body in the tract during movement.

The first driving unit, the second driving unit and the third driving unit are respectively internally provided with a first fluid accommodation cavity suitable for accommodating a fluid; and the first fluid accommodation cavity is communicated with a fluid supply-drainage device through a first fluid supply-drainage pipe, and under an action of the fluid supply-drainage device, able to extend when pressurized or contract when depressurized along the axis.

The first fluid accommodation cavity is formed in the peripheral wall of the tube, with one end connected with the first fluid supply-drainage pipe.

The first driving unit, the second driving unit and the third driving unit respectively comprise at least one first expansion body, for the first fluid accommodation cavity to be formed therein.

The tube is provided with expansion cavities evenly along the circumference thereof, for the first expansion body to be arranged therein.

The propelling structure further comprises a first restraint layer, which circumferentially surrounds an exterior of the tube, for restricting the extension or contraction of the first driving unit, the second driving unit and the third driving unit along the axis of the tube.

The first restraint layer circumferentially surrounds exteriors of the first driving unit, the second driving unit and the third driving unit respectively, for restricting the extension or contraction thereof along the axis of the tube.

The support structure includes a positioning and expansion unit, fixedly arranged on the peripheral wall of the tube, adapted for expanding or contracting in an radial direction of the tube, and able to be fixed to the tract when expanding, and separated from the tract when contracting; and a second restraint layer, surrounding the exterior of the positioning and expansion unit along an circumference of the tube, for restricting the expansion or contraction of the positioning and expansion unit in an radial direction of the tube.

The positioning and expansion unit is provided with a second fluid accommodation cavity which is suitable for accommodating a fluid and is communicated with the fluid supply-drainage device through a second fluid supply-drainage pipe; the second fluid accommodation cavity is annular.

The support structure further comprises a negative-pressure positioning device which is arranged on the tube and adapted for enabling the self-propelled soft robot body to be absorbed on the tract via negative pressure, the negative-pressure positioning device comprises:

negative-pressure holes, evenly arranged on the peripheral wall of the tube and communicated with the tract; and a negative pressure conduit, connecting the negative-pressure holes with the fluid supply-drainage device, so as to connect negative-pressured branches.

The self-propelled soft robot body further comprising an outer cover which covers exteriors of the propelling structure and the support structure, and the outer cover is made of flexible material.

The self-propelled soft robot body further comprising a detection device which further comprises a pressure sensor, circumferentially and evenly arranged on an outer side of the support structure, adapted for detecting a pressure imposed on the tract by the support structure; and a tension sensor, circumferentially and evenly arranged on an outer side of the propelling structure, adapted for detecting a protraction or contraction state of the propelling structure.

The technical solution of the present disclosure has the following advantages:

1. The self-propelled soft robot body provided by the present disclosure is adapted for automatically walking in a human tract, including a tube, at least one propelling structure and at least two support structures, the propelling structure includes a first driving unit, a second driving unit and a third driving unit, which are evenly fixed on a peripheral wall of the tube cavity, relative to an axis thereof, and along the axis of the tube; and the first driving unit, the second driving unit and the third driving unit are respectively telescopic along the axis of the tube; the second driving unit and the third driving unit evenly distributed along an axis in the tube can achieve protraction on an expanded side and contraction on an unexpanded or contracted side respectively when expanding along the axis of the tube, and the propelling structure bends towards the unexpanded or contracted side, thereby realizing free steering of the self-propelled soft robot body in the human tract. Overall protraction, torsional protraction, decompressed contraction and bending of the propelling mechanism in any direction are achieved by controlling the axial protraction or contraction of the three driving units. In comparison with the arrangement of a rigid steering device such as a line-driven structure in an endoscope for steering in the prior art, the structure of the propelling device of the self-propelled soft robot body provided by the present disclosure is free of hard objects, and improves human comfort and operational safety. The support structures are located at both ends of the propelling structure, at least one propelling structure is arranged between every two adjacent support structures, the support structures are fixedly connected with the propelling structure, arranged on the peripheral wall of the tube cavity, and adapted for fixing at least one end of the self-propelled soft robot body in the human tract, and provides support for the self-propelled soft robot body during the movement in the tract. Through the coordinated movement of the support structure and the propelling structure at both ends, it can provide support for the expansion and steering movement of the propelling structure, realizing worm-type autonomous propulsion of the self-propelled soft robot body in the human tract, reducing the difficulty in operating the soft robot body. In addition, since the robot body does not contain rigid components or ferromagnetic components, the robot body has the advantage of magnetic compatibility, and can realize intraoperative real-time navigation during magnetic resonance imaging.

2. The present disclosure provides a self-propelled soft robot body, wherein the first driving unit, the second driving unit and the third driving unit are respectively internally provided with a first fluid accommodation cavity suitable for accommodating a fluid, the first fluid accommodation cavity is formed in the peripheral wall of the tube and communicated at one end with a fluid supply-drainage device, the axial protraction or contraction of the driving unit can be achieved by pressing fluid into or withdrawing fluid from the first fluid accommodation cavity. The first fluid accommodation cavity is connected to the external fluid supply-drainage device under control, which can control combined or individual axial protraction or contraction of each driving units, realizing precise control of various walking postures of the self-propelled soft robot body.

3. The present disclosure provides a self-propelled soft robot body, wherein the propelling structure includes three driving units distributed evenly along the circumference of the tube. Compared with the technical solution of a propelling mechanism which can only protract or contract in the prior art, it is possible to provide more attitude changes for the propelling structure through the arrangement of a plurality of evenly distributed driving units, so as to achieve a change in the angle of the propelling structure, enabling the soft robot body to adjust the direction of movement in three-dimensional space, allowing more actions in the tract, and realizing free movement in a multi-branch tract and a curved tract, to adapt to the complex environment thereof.

4. The present disclosure provides a self-propelled soft robot body, wherein two propelling structures are arranged along an axis of the tube, three support structures are respectively arranged at both ends and the middle part of the propelling structure. The alternative fixation of the propelling structures at both ends and the three support structures on the tube can provide more freedom of motion for the self-propelled soft robot body in a human tract, making it adaptable to the complex bending changes of tract. The three support structure can provide more support points for the propelling structure, reduce the force on the tract wall, and reduce the operational risk. Meanwhile, the self-propelled soft robot body of the structure implements the modular setting of the propelling structures and support structures, and also allows more support structures and propelling structures to be combined, enabling the self-propelled soft robot body to have a more diversified propulsion manner and more flexible movement, rendering obvious simulation effect. Therefore, the self-propelled soft robot body adapts to the complicated environment in the tract while reducing the risks.

5. The present disclosure provides a self-propelled soft robot body, the propelling structure further comprises a first restraint layer, which circumferentially surrounds an exterior of the tube, for restricting the extension or contraction of the first driving unit, the second driving unit and the third driving unit along the axis of the tube. The first restraint layer is used to limit the expansion direction of the driving unit on the propelling structure. And in comparison to using a spring or a collapsible tube to limit the direction of deformation in the prior art, in the present disclosure, the propelling structure wrapped in the first restraint layer has a flatter and smoother surface, causing minor injuries to the wall of the human tract. And the first restraint layer is made of fabric with soft texture that is less dangerous.

6. The present disclosure provides a self-propelled soft robot body, the first restraint layer circumferentially surrounds exteriors of the first driving unit, the second driving unit and the third driving unit respectively, for restricting the extension or contraction thereof along the axis of the tube. The first restraint layer is respectively wrapped on the outside of the driving unit, so as to impose more accurate limitation effect for each driving unit, and the first restraint layer may be wound around each of the driving units in different manners, thus realizing the combination of a variety of movements, such as shortening or twisting of the propelling structure.

7. The present disclosure provides a self-propelled soft robot body, wherein the support structure includes: a positioning and expansion unit, fixedly arranged on the peripheral wall of the tube, adapted for expanding or contracting in an radial direction of the tube, and able to be fixed to the tract when expanding, and separated from the tract when contracting; a second restraint layer, surrounding the exterior of the positioning and expansion unit along an circumference of the tube, for restricting the expansion or contraction of the positioning and expansion unit in an radial direction of the tube. When used, the positioning and expansion unit can expand to be clamped in the tract, so that one or both ends of the propelling structure can be fixed at a certain position in the tract to realize the rest detection of the soft robot body, or provide a rest point for the expansion and steering of the propelling structure, allowing the self-propelled soft robot body to automatically walk inside the tract.

8. The present disclosure provides a self-propelled soft robot body, wherein the support structure further includes a negative-pressure positioning device which is arranged on the tube and adapted for enabling the self-propelled soft robot body to be absorbed on the tract via negative pressure, the negative-pressure positioning device includes: negative-pressure holes, evenly arranged on the peripheral wall of the tube and communicated with the tract; and a negative pressure conduit, connecting the negative-pressure holes with the fluid supply-drainage device, so as to connect negative-pressured branches. The negative-pressure positioning device can utilize negative pressure to allow the negative-pressure holes to be absorbed on the wall of the tract, so as to achieve a good fixation effect. When used along with the positioning and expansion unit, the self-propelled soft robot body can be fixed with the aid of a negative-pressure positioning device, in the case that the tract has a large diameter and the positioning and expansion unit cannot be fixed.

9. The present disclosure provides a self-propelled soft robot body, which further includes an outer cover which covers exteriors of the propelling structure and the support structure, and the outer cover is made of flexible material. The use of an outer cover made of a flexible material can reduce stimulus to the human tract, prevent leakage of the fluid from the fluid cavity which will contaminate the human tract otherwise, and protect and maintain a sterile environment.

10. The present disclosure provides a self-propelled soft robot body, including a detection device, which includes: a tension sensor, arranged on the propelling structure, able to detect a protraction state of the propelling structure; a pressure sensor, arranged on the support structure, able to detect a pressure imposed on the tract by the support structure. By using the above-mentioned sensors, data about the inside situation of tract and the state of acting forces between the self-propelled soft robot body and the tract can be obtained in time, and then the acquired data can be fed back to a processing department for processing, before being converted into mechanical control signals and sent to each execution department. In this way, the motion state of the self-propelled soft robot body can be adjusted in time to realize the intelligent movement of the self-propelled soft robot body.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

In order to make a clearer description of technical solutions in specific implementations of the present disclosure or prior art, drawings involved in description for the specific implementations or the prior art will be briefly introduced, and apparently, the drawings described below illustrate some implementations of the present disclosure, for one with ordinary skill in the art, other drawings can also be obtained in accordance with these drawings without delivering creative efforts.

DESCRIPTION FOR REFERENCE NUMERALS

2—tube; 3—propelling structure; 4—support structure; 5—tube-wire portion; 6—fluid supply-drainage device; 7—detection device; 8—control system; 11—connection end; 12—detection end; 21—tube cavity; 31—first driving unit; 32—second driving unit; 33—third driving unit; 34—first restraint layer; 35—first expansion body; 36—expansion cavity; 37—first fluid accommodation cavity; 38—first fluid supply-drainage pipe; 41—positioning and expansion unit; 42—second restraint layer; 43—negative-pressure positioning device; 44—second fluid supply-drainage pipe; 45—second fluid accommodation cavity; 71—pressure sensor; 72—tension sensor; 121—spherical tip; 122—instrument connector s; 123—connector for pipelines; 124—CCD camera; 431—negative-pressure hole; 432—negative pressure conduit.

DETAILED DESCRIPTION

Technical features involved in different implementations described in the present disclosure below may be combined with each other as long as no conflicts occur therebetween.

Embodiment 1

Figure 1:
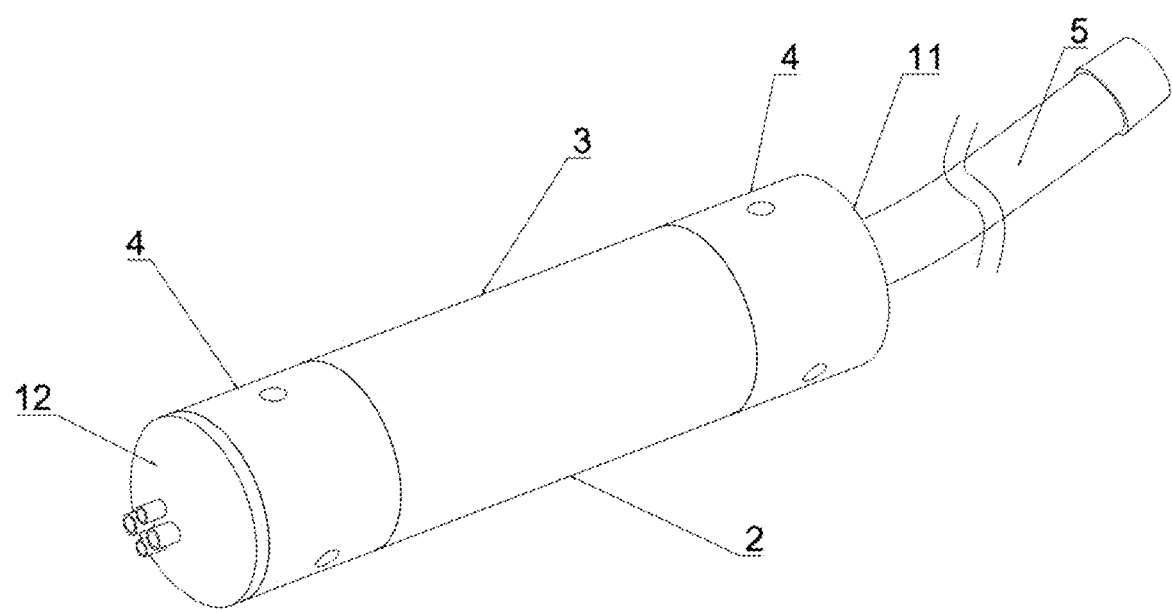
FIG. 1 is a stereogram for a self-propelled soft robot body provided in embodiment 1 of the present disclosure.
Figure 2:
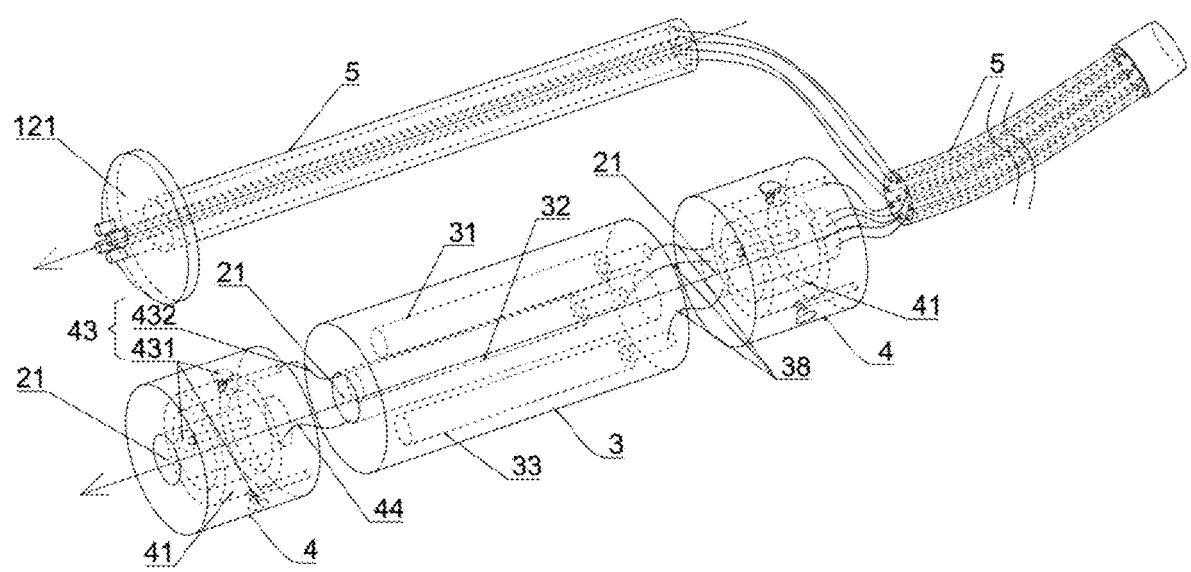
FIG. 2 is an exploded view for a self-propelled soft robot body provided in embodiment 1.
Figure 6:
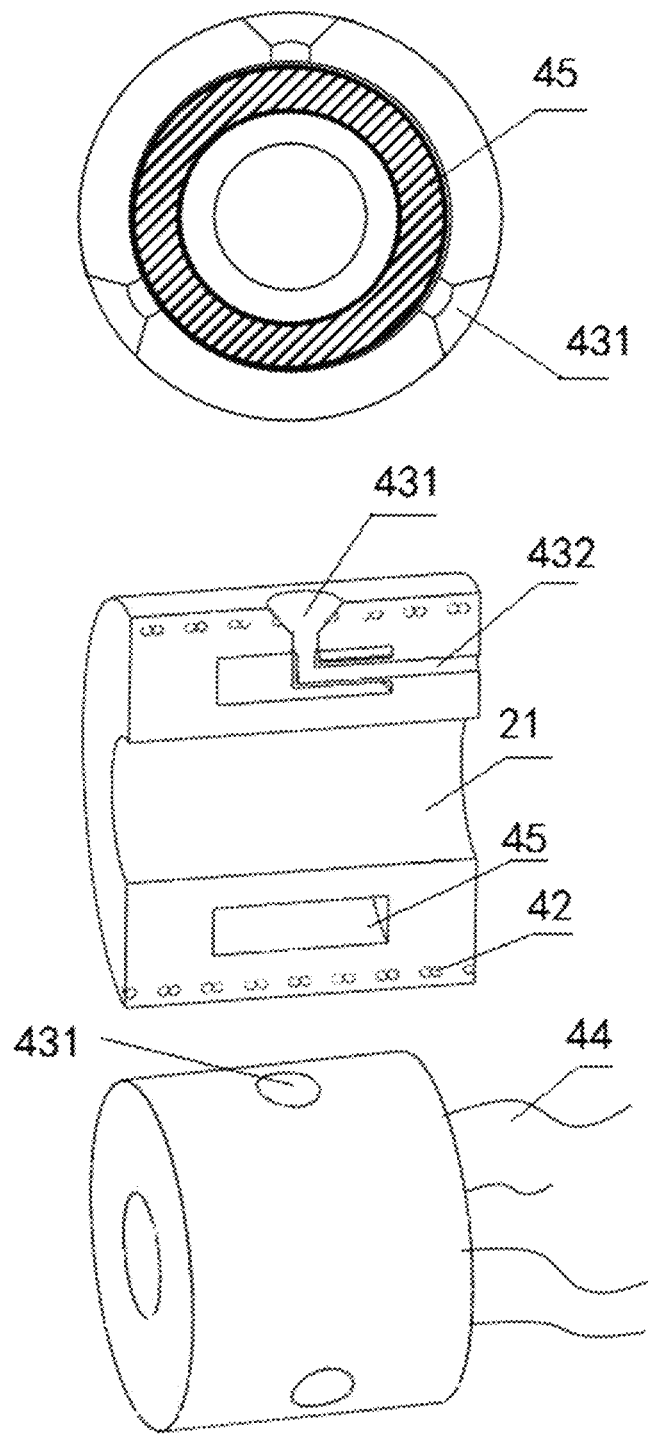
FIG. 6 is a structural diagram for a support structure in embodiment 1.
Figure 7:
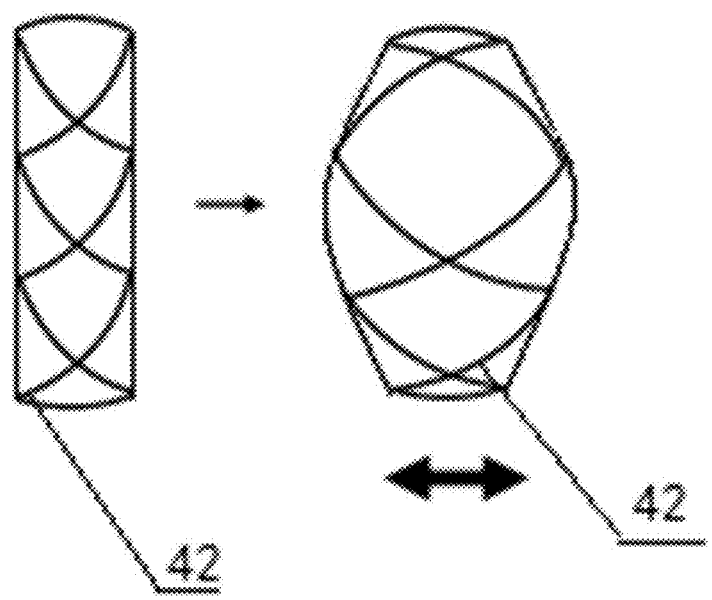
FIG. 7 is a diagram showing a winding mode of a second restraint layer in embodiment 1.
Figure 8:
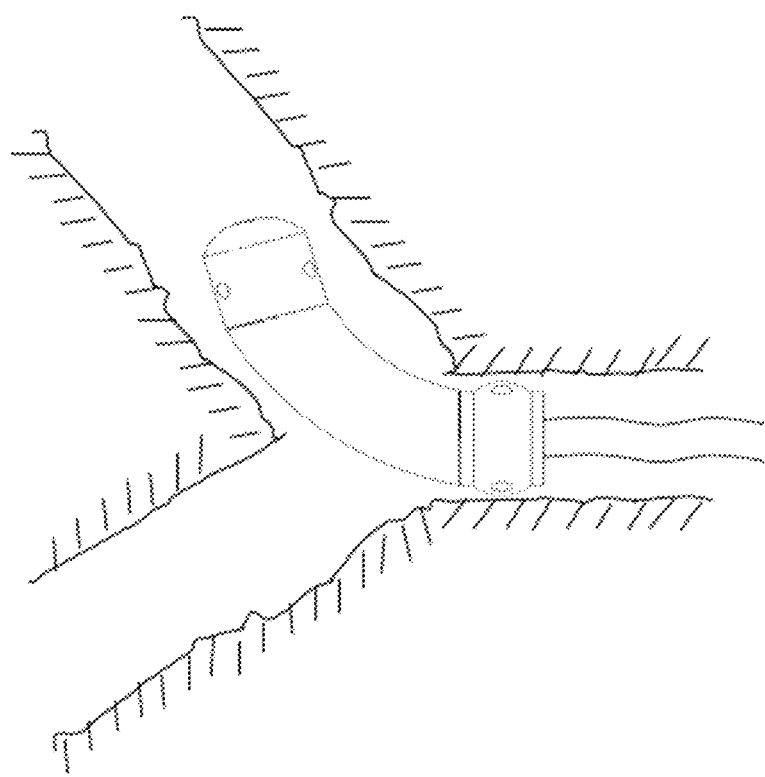
FIG. 8 is a diagram showing the steering of the self-propelled soft robot body in a tract in embodiment 1.

This embodiment provides a soft robot body, which has a structure as shown in FIG. 1 to FIG. 11, and is adapted for automatically moving in a tract, including a tube 2, a propelling structure 3, a support structure 4, the tube 2 is internally and axially provided with a tube cavity 21, as shown in FIG. 2, the propelling structure 3 includes a first driving unit 31, a second driving unit 32 and a third driving unit 33, which are evenly fixed on a peripheral wall of the tube cavity 21, relative to an axis thereof, and along the axis of the tube 2, the first driving unit 31, the second driving unit 32 and the third driving unit 33 are respectively telescopic along the axis of the tube 2. As shown in FIG. 8, the second driving unit 32 and the third driving unit 33 evenly distributed along an axis in the tube 2 can achieve protraction on an expanded side and contraction on an unexpanded or contracted side respectively when expanding along the axis of the tube 2, and the propelling structure 3 bends towards an unexpanded or contracted side, thereby realizing free steering of the self-propelled soft robot body in the human tract. Overall protraction, torsional protraction, decompressed contraction and bending of the propelling mechanism in any direction are achieved by controlling the axial protraction or contraction of the three driving units. In comparison with the arrangement of a rigid steering device such as a line-driven structure in an endoscope for steering in the prior art, the structure of the propelling device of the self-propelled soft robot body provided by the present disclosure is free of hard objects, and improves human comfort and operational safety. In addition, the soft robot body does not contain rigid parts and ferromagnetic parts, so the robot body has the advantage of magnetic compatibility, and can realize real-time navigation during surgery under magnetic resonance imaging. In addition, the soft robot body does not contain rigid parts and ferromagnetic parts, so the robot body has the advantage of magnetic compatibility, and can realize real-time navigation during surgery under magnetic resonance imaging.

As shown in FIG. 1 and FIG. 2, a support structure 4 is located at both ends of the propelling structure 3, a propelling structure 3 is arranged between every two adjacent support structures 4. The support structure 4 is fixedly connected to the propelling structure 3, and is arranged on a peripheral wall of the tube cavity 21, suitable for fixing at least one end of the self-propelled soft robot body to the tract, and to provide support for the self-propelled soft robot body during movement within the tract. Through the coordinated movement of the support structure 4 and the propelling structure 3 at both ends, the disclosure can provide support for the telescopic movement of propelling structure 3 and achieve worm-type autonomous advancement of the self-propelled soft robot body in the tract, reducing the operating difficulty thereof.

The propelling structure 3 and the support structure 4 can be arranged in various numbers. In this embodiment, the self-propelled soft robot body comprises one propelling structure 3 and two support structures 4.

Specifically, in this embodiment, the tube 2 is made of a silicone material, or other flexible materials with human-affinity. The processing method can be filling with a mold, or direct 3D printing.

Figure 3:
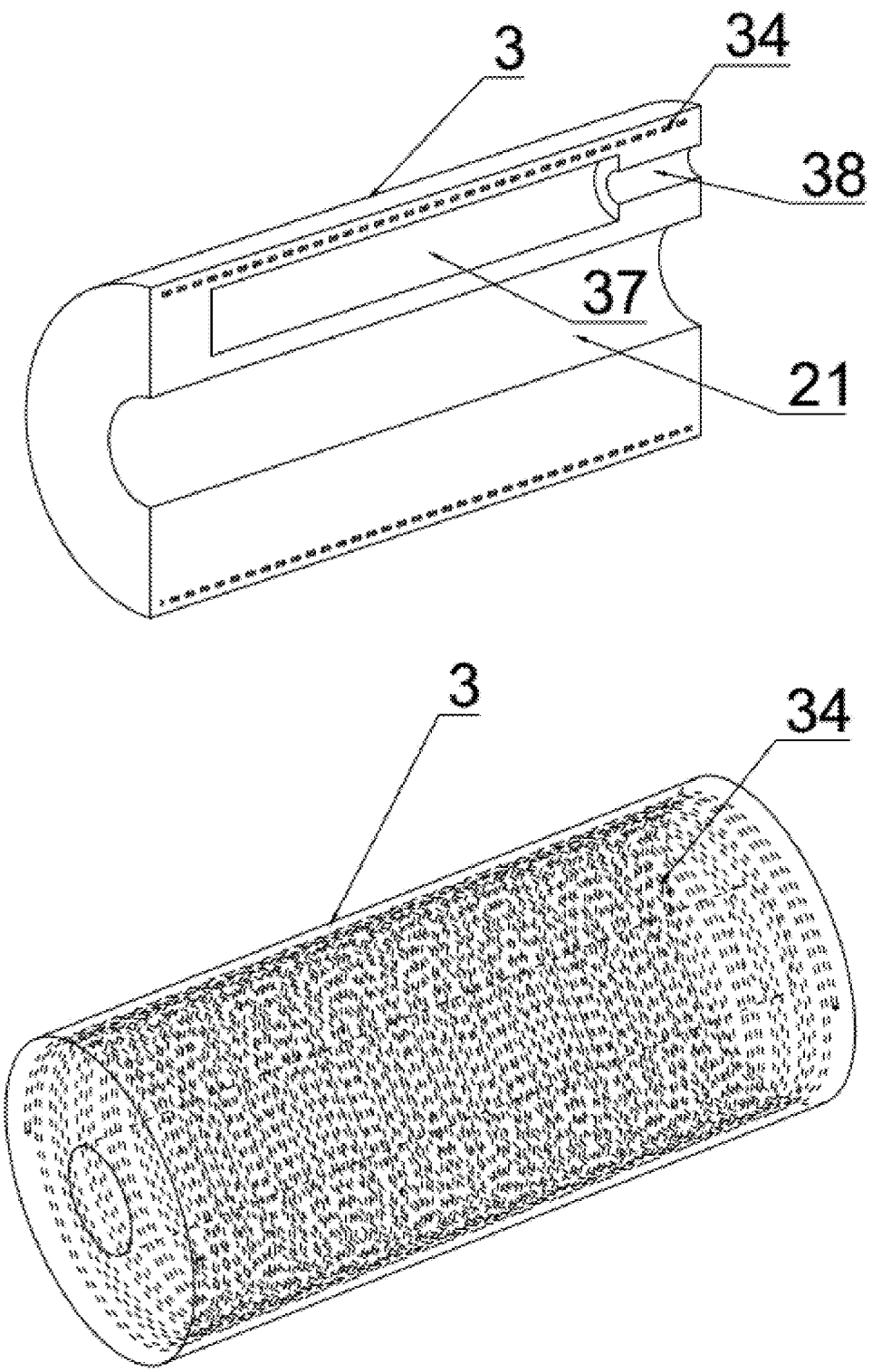
FIG. 3 is a longitudinal section illustrating the arrangement of a first restraint layer of the propelling structure in embodiment 1.

As shown in FIG. 2 and FIG. 3, the first driving unit 31, the second driving unit 32, and the third driving unit 33 in this embodiment are respectively internally provided with a first fluid accommodation cavity 37 suitable for accommodating a fluid, the first fluid accommodation cavity 37 is communicated with a fluid supply-drainage device 6 through a first fluid supply-drainage pipe 38, and is able to extend when pressurized or contract when depressurized along the axis, under an action of the fluid supply-drainage device 6.

As shown in FIG. 3, in this embodiment, the first fluid accommodation cavity 37 is formed in the peripheral wall of the tube 2, with one end connected with the first fluid supply-drainage pipe 38. By pressing fluid into or discharging fluid from the first fluid accommodation cavity 37, expansion and contraction of the driving unit can be achieved. The first fluid accommodation cavity 37 is connected to the external fluid supply-drainage device 6 under control, so as to control combined or individual extension or contraction of each driving unit, achieving precise control of various walking postures of self-propelled soft robot body.

In this embodiment, a gas is used as a filling material, i.e., in this embodiment the fluid is a gas, and the fluid supply-drainage device 6 is a gas pressure pump. As an alternative implementation, the fluid may also be a liquid.

As shown in FIG. 3, in this embodiment, the propelling structure 3 further comprises a first restraint layer 34, which circumferentially surrounds an exterior of the tube 2, for restricting the extension or contraction of the first driving unit 31, the second driving unit 32 and the third driving unit 33 along the axis of the tube 2. And in comparison to using a spring or a collapsible tube to limit the direction of deformation in the prior art, in the present disclosure, the first restraint layer 34 is used to restrict the expansion direction of the driving unit on the propelling structure 3, the propelling structure wrapped in the first restraint layer has a flatter and more smooth surface, causing minor injuries to the wall of the human tract. And the first restraint layer 34 is made of fabric with soft texture that is less dangerous.

Figure 4:
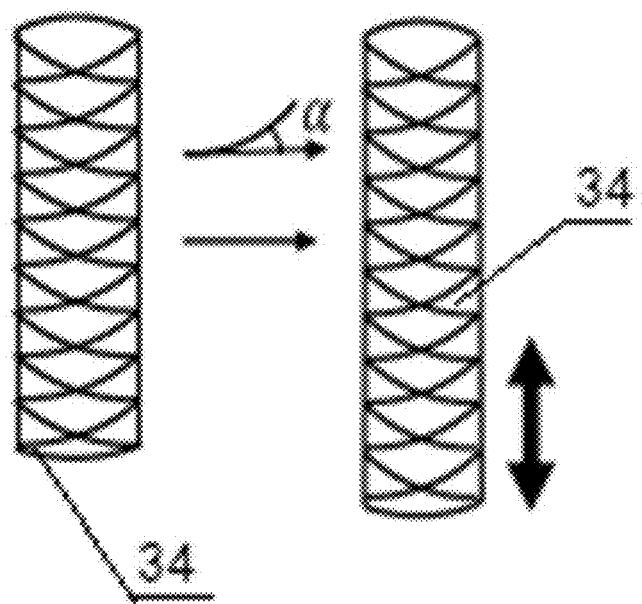
FIG. 4 is a diagram showing a first winding mode of the first restraint layer in embodiment 1.

Specifically, in this embodiment, the first restraint layer 34 is wound in a manner as shown in FIG. 4. The fiber is clockwise or counterclockwise symmetrically wound, with an inclination angle α ranging from 0° to 40°. The driving unit or tube covered by the fiber is restricted to axial extension only, and cooperates with the gas pressure pump to provided different air pressure to each driving unit, achieving an effect of bending and elongating the propelling structure 3 simultaneously. When each driving unit has the same internal air pressure, an effect of overall elongation is achieved.

Figure 5:
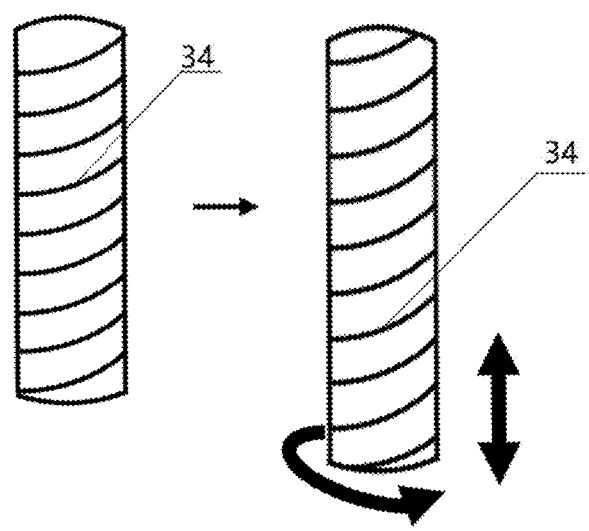
FIG. 5 is a diagram showing a second winding mode of the first restraint layer in embodiment 1.

As an alternative implementation, in this embodiment, the first restraint layer 34 can also be wound in a manner as shown in FIG. 5. The fiber is wound clockwise or counterclockwise in one direction, with an inclination angle ranging from 0° to 40°. When the gas pressure pump provides air pressure to the driving unit, the driving unit or tube covered by the first restraint layer 34 wound in this way extends along the axis and twists around the axis, so that the tube realizes movement through axial torsional elongation.

As shown in FIG. 6, in this embodiment, the support structure 4 comprises: a positioning and expansion unit 41 and a second restraint layer 42, the positioning and expansion unit 41 is fixedly arranged on the peripheral wall of the tube 2, adapted for expanding or contracting in an radial direction of the tube 2, and able to be fixed to the tract when expanding, and separated from the tract when contracting; and a second restraint layer 42, surrounding the exterior of the positioning and expansion unit 41 along an circumference of the tube 2, adapted for restricting the expansion or contraction of the positioning and expansion unit 41 in an radial direction of the tube 2. The positioning and expansion unit 41 is provided with an annular second fluid accommodation cavity 45 which is suitable for accommodating a fluid and is communicated with the gas pressure pump through a second fluid supply-drainage pipe 44. The gas pressure pump imposes pressure in the second fluid accommodation cavity 45, so that the positioning and expansion unit 41 radially expands to be clamped in the tract, enabling one or both ends of the propelling structure 3 to be fixed at a certain position in the tract to realize rest detection of the soft robot body, or provide a rest point for the expansion and contraction of the propelling structure 3, allowing worm-like automatic advancement of the soft robot body in the tract.

In this embodiment, the second restraint layer 42 is made of soft woven fiber which is wound in a manner as shown in FIG. 7, wherein the fiber is clockwise and counterclockwise symmetrically wound, with a winding angle α ranging from 60-90°. The positioning and expansion unit 41 covered by the fiber is restricted to axial extension only, allowing it to be clamped.

As shown in FIG. 6, in this embodiment, the support structure 4 also comprises a negative-pressure positioning device 43 which is arranged on the tube 2 and adapted for enabling the self-propelled soft robot body to be absorbed on the tract via negative pressure, the negative-pressure positioning device 43 comprises negative-pressure holes 431, evenly arranged on the peripheral wall of the tube 2 and communicated with the tract; and a negative pressure conduit 432, connecting the negative-pressure holes 431 with the fluid supply-drainage device 6, so as to connect negative-pressured branches. The negative-pressure positioning device 43 uses negative pressure for enabling the negative-pressure hole 431 to be absorbed on the tract wall, achieving a good fixation effect. When used along with the positioning and expansion unit 41, the self-propelled soft robot body can be fixed with the aid of a negative-pressure positioning device, in the case that the tract has a large diameter and the positioning and expansion unit 41 cannot be fixed.

Specifically, as shown in FIG. 6, the negative-pressure holes 431 in this embodiment are arranged on the outer wall of tube 2 where the positioning and expansion unit 41 is located, and 3 negative-pressure holes are uniformly distributed along the tube 2.

As an alternative implementation, the support structure 4 can be only provided with the negative-pressure positioning device 43 to position one end of the soft robot body, and is suitable for use in thin tracts, to prevent the positioning and expansion unit 41 from generating a large interaction force on the tract wall when it expands, and thus preventing dangers.

Figure 9:
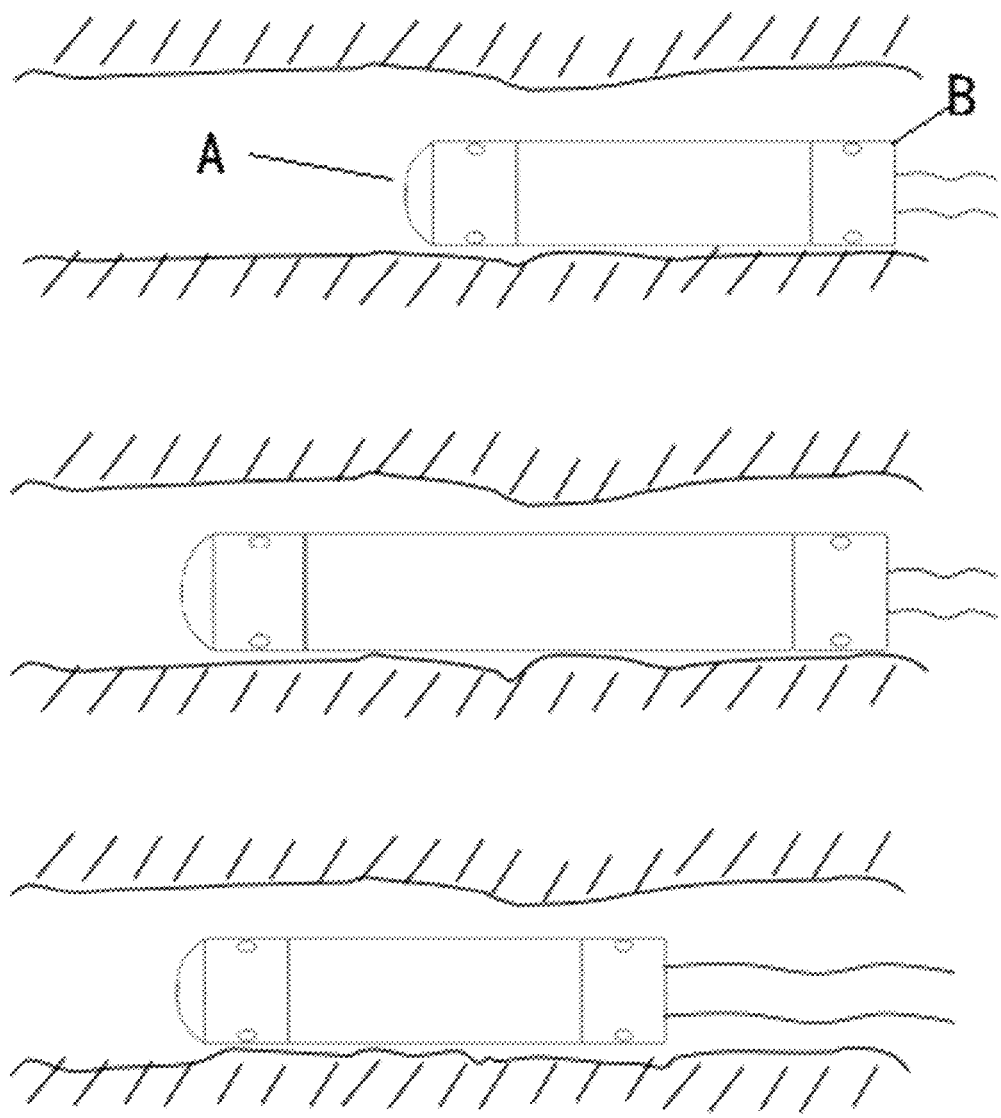
FIG. 9 is a diagram showing the walking process of the self-propelled soft robot body in embodiment 1.

Specifically, assuming the end of the support structure 4 entering the tract firstly as a positioning end A, and the end entering the tract afterwards as a positioning end B. As shown in FIG. 9, the movement process of the soft robot body in this embodiment in the tract is as follows:

Stage 1, the positioning end B is fixed on the wall of the tract via inflation or negative pressure absorption, and both the propelling structure 3 and the positioning end A maintain a natural state.

Stage 2, the positioning end B remains clamped, the positioning end A keeps the natural state, the propelling structure 3 extends forward or turns around via inflated expansion, and push the positioning end A to move forward.

Stage 3, the positioning end B and the propelling structure 3 respectively remain clamped and elongated, and the positioning end A is fixed to the tract wall via inflated expansion or negative pressure adsorption;

Stage 4, the positioning end B releases pressure to be detached from the tract wall, and both the propelling structure 3 and the positioning end A respectively remain clamped and elongated;

Stage 5, the positioning end B maintain the natural state, the positioning end A remains clamped, the propelling structure 3 releases pressure to contract forward, driving the positioning end B to move forward;

Stage 6, the positioning end B is fixed on the wall of the tract via inflated expansion or negative pressure absorption, the propelling structure 3 maintain the natural state, and the positioning end A remains clamped;

So far, this cyclic process is repeatedly performed, so that the soft robot body moves forward continuously, and vice versa.

As shown in FIG. 1 and FIG. 2, the soft robot body in this embodiment comprises a detection end 12 that first enters the tract and a connection end 11 that connects to the tube-wire portion 5 opposite to the detection end 12. The detection end 12 is provided with a spherical tip 121 which is connected to the tube-wire portion 5. The tube-wire portion 5 passes through the tube cavity 21 and extends through the connection end 11 to the external gas pressure pump and other equipment. The tube 2 at the portion where the support structure 4 of the detection end 12 is located is fixedly connected to the internal tube-wire portion 5 and the remaining tube 2 is only sleeved on the outside of the tube-wire portion 5, and can slide relative to the tube-wire portion 5. When moving over the tube 2, the propelling structure 3 and the support structure 4 drive the internal tube-wire portion 5 to move inside the tract.

As shown in FIG. 2, in this embodiment the tube-wire portion 5 includes a working channel through which surgical instruments can pass and driving channels connected the propelling structure 3 and the support structure 4; the first fluid supply-drainage pipe 38, the second fluid supply-drainage Pipe 44 and the negative pressure conduit 432 pass through the driving channel respectively to be connected to the propelling structure 3, the support structure 4, and the negative-pressure positioning device 43.

Figure 10:
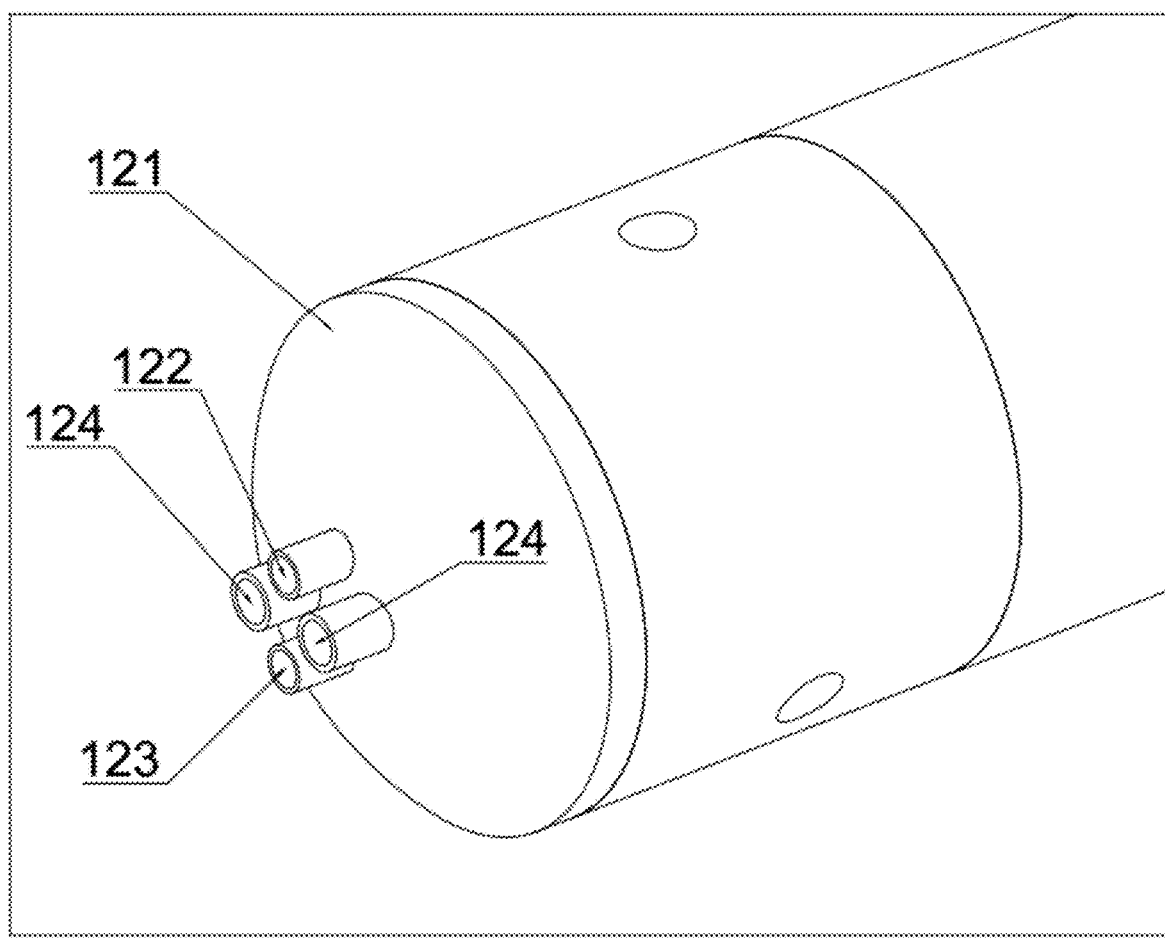
FIG. 10 is a stereogram for a spherical tip in embodiment 1.

Wherein, the working channel contains a plurality of pipes arranged in the tube-wire portion which are suitable for accommodating sensors, cameras, gas and water supplies, and operating instruments, etc., so as to realize front-end pressure measurement and collection and detection of material components in the pipes, as well as operations such as image acquisition, gas supply and water supply in the pipeline, and allowing introduction of instruments to achieve clamping and pipeline cleaning. As shown in FIG. 10, the spherical tip 121 of the detection end 12 is provided with a mini CCD camera 124 with integrated lighting function and an instrument connector 122 connected with the working channel, pipeline connector 123, etc. In the working channel, a variety of medical devices such as biopsy forceps, electrosurgical tools, physiological saline syringes, etc. can be used to enter the tract through the instrument connector 122 for operation. The pipeline connector 123 is connected to the delivery tube arranged in the working channel to achieve the delivery or injection of related drugs. Specifically, as shown in FIG. 10, the CCD camera 124 in this embodiment is installed in a pipe opening of the working channel formed at the spherical tip (such as the cylindrical protruding portion shown in FIG. 10), and one CCD camera 124 is arranged on both the right and the lift symmetrically to form a binocular camera, and is connected to an external control system 8 through a data connection line provided in the working channel. In this way, a stereo image of the front of the soft robot body is generated, facilitating an operator to judge the environment of the tract.

In this embodiment, the soft robot body further includes an outer cover, which covers exteriors of the propelling structure 3 and the support structure 4. An outer cover made of a flexible material can reduce stimulation to the tract, prevents leakage of the fluid from the fluid cavity and thus contamination to the tract, and protect and maintain a sterile environment.

Figure 11:
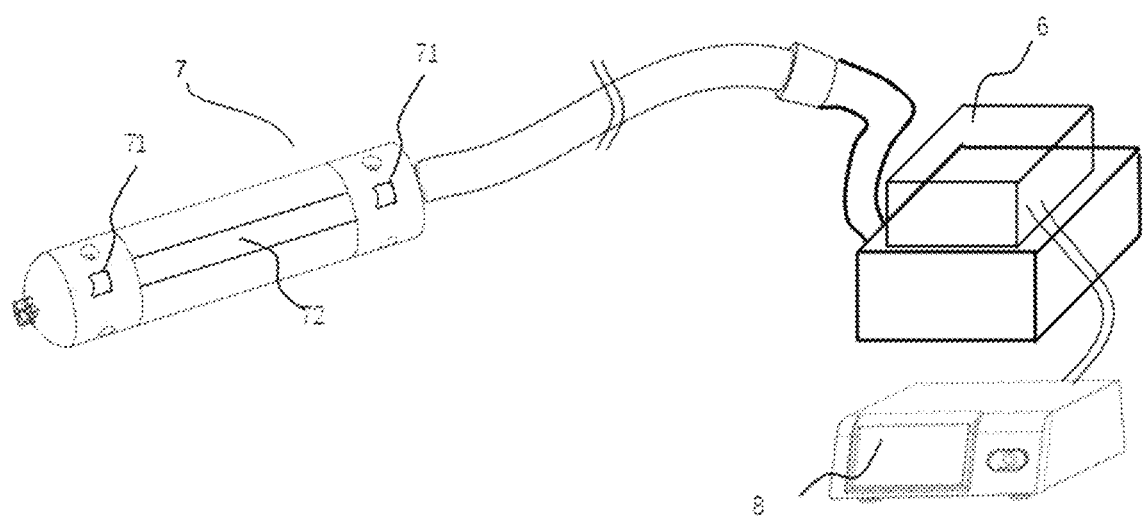
FIG. 11 is a diagram showing the connection between a control system and the self-propelled soft robot body in embodiment 1.

As shown in FIG. 11, the soft robot body in this embodiment is also provided with a detection device 7 which further comprises a pressure sensor 71, the pressure sensor 71 is circumferentially and evenly arranged on an outer side of the support structure 4, adapted for detecting a pressure imposed on the tract by the support structure 4; and a tension sensor 72, circumferentially and evenly arranged on an outer side of the propelling structure 3, adapted for detecting a protraction or contraction state of the propelling structure 3. Using the above-mentioned sensors, the situation in the front tract of detection end 12 and the status of the force between the soft robot body and the tract can be known in time, and then the acquired data can be fed back to the processing department for processing, converted into mechanical control signals, and sent to each execution department, so as to adjust the movement status of the soft robot body in time to realize the intelligent movement of the soft robot body.

In this embodiment, the soft robot body further includes a control system 8, which is connected to the soft robot body and the gas pressure pump, and is used to process various data information sent by detection device 7. The image data collected by the CCD camera 124 can also be used to automatically identify the tract environment, and make adjustments to the direction of movement of the soft robot. The pressure data obtained by the pressure sensor 71 can be used to automatically adjust the air pressure applied by the gas pressure pump to prevent damage caused by excessive expansion to tract. And the data obtained by the tension sensor 72 can be used to determine the current elongation or bending status of the soft robot body in time. Then mechanical control data are sent to the gas pressure pump, to adjust the air pressure in the propelling structure 3, realizing bending and steering of the soft robot body.

Embodiment 2

This embodiment provides a self-propelled soft robot body, which differs from embodiment 1 in that, the first restraint layer 34 in this embodiment circumferentially surrounds exteriors of the first driving unit (31), the second driving unit (32) and the third driving unit (33) respectively, for restricting the extension or contraction thereof along the axis of the tube (2). As shown in FIG. 11, the first restraint layer 34 respectively cover the outsides of the driving unit, exerting a more accurate restriction effect to each driving unit. At the same time, each driving unit may be provided with a first restraint layer 34 wound in different manners, realizing a combination of multiple motions such as elongation and contraction or twisting of the propelling structure 3.

Embodiment 3

Figure 12:
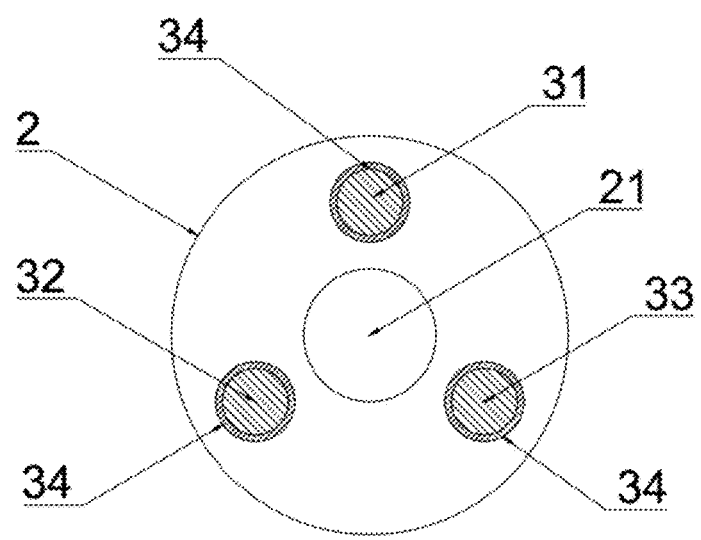
FIG. 12 is a transversal section of a propelling structure in embodiment 2.
Figure 13:
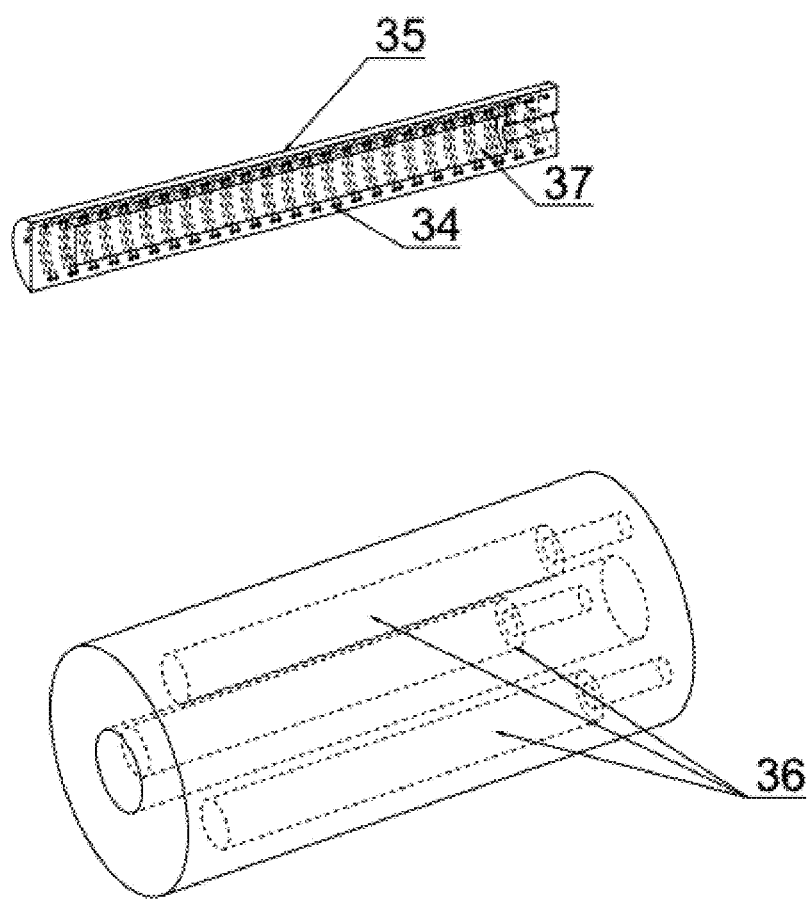
FIG. 13 is a diagram of a propelling structure in embodiment 3.

As shown in FIG. 13, this embodiment provides a self-propelled soft robot body, which is different from the main propelling type soft robot body in embedment 1 in that, the first driving unit 31, the second driving unit 32, and the third driving unit 33 are respectfully provided with a first expansion body 35, and a first fluid accommodation cavity 37 is formed in first expansion body 35. Specifically, as shown in FIG. 12, the peripheral wall of tube 2 is circumferentially and evenly provided with three expansion cavities 36, for the three first expansion bodies 35 to be respectively placed therein, and the shape of each first expansion body 35 is matched with that of the expansion cavity 36, to form the first driving unit 31, the second driving unit 32 and the third driving unit 33. A first fluid accommodation cavity 37 is provided inside each first expansion body 35, and one end of the first fluid accommodation cavity 37 is connected to a first fluid supply-drainage pipe 38 formed in the first expansion body. When fluid enters the first fluid accommodation cavity 37, the first expansion body 35 expands, causing the expansion cavity 36 to deform, which in turn causes the deformation of the tube 2 at the position of the expansion cavity 36. The driving unit of this structure realizes replacement of the expansion body, so as to prevent scrapping of the entire tube 2 due to damage to a single driving unit.

Correspondingly, as shown in FIG. 13, the first restraint layer 34 in this embodiment is wound in the outer wall of the first expansion body 35 to limit the expansion direction of the first expansion body 35. Of course, the first restraint layer 34 can also be wound around the exterior of the tube 2 where the propelling structure 3 is located.

As an alternative implementation, in this embodiment, the expansion cavity of the first driving unit 31, second driving unit 32, and third driving unit 33 can also be internally and respectively provided with multiple expansion bodies. The coordinated expansion of multiple expansion bodies achieves the steering of a single driving unit in more angles, improving the flexibility thereof and varying movement postures.

Embodiment 4

This embodiment provides a self-propelled soft robot body, which is different from embodiment 1 in that, the propelling structure 3 includes more than three driving units circumferentially and evenly arranged along the tube 2. Compared with the technical solution in which the propulsion mechanism can only extend axially and linearly in the prior art, the even arrangement of a plurality of driving units can provide more attitude changes for the propelling structure 3 and realize the angle change of the propelling structure 3, so that the soft robot body can adjust the direction of movement in a three-dimensional space, allowing more movements in the tract, as well as free movement in the multi-branch and curved tract, to adapt to the complex environment of the tract.

Embodiment 5

Figure 14:
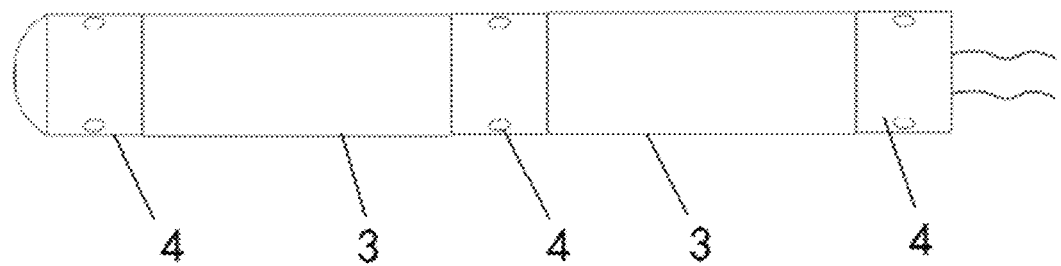
FIG. 14 is a compositional diagram for a self-propelled soft robot body in embodiment 5.

This embodiment provides a self-propelled soft robot body, as shown in FIG. 14, with a structure differing from that of the soft robot body in embedment 1 in that, the soft robot body in this embodiment is provided axially along the tube 2 with two propelling structures 3 and three support structures 4, the three support structures 4 are respectively arranged at both ends and the middle part of the two propelling structures 3. The alternative fixation of the two propelling structures 3 and three support structures 4 on the tube can provide more freedom of motion for the self-propelled soft robot body in a tract, making it adaptable to the complex bending changes of tract. The three support structures 4 can provide more support points for the propelling structure 3, reducing the concentrated force of unilateral support structure 4 on the tract wall, and reducing the risk of tract perforation. At the same time, the soft robot body of this structure realizes modular arrangement of the propelling structures 3 and the support structures 4, enabling more support structures 4 and propelling structures 3 to be combined, diversifying propelling manners of the soft robot body, making the movement more flexible and the simulation effect more obvious, so as to adapt to the complex environment of tract while reducing the risk.

Figure 15:
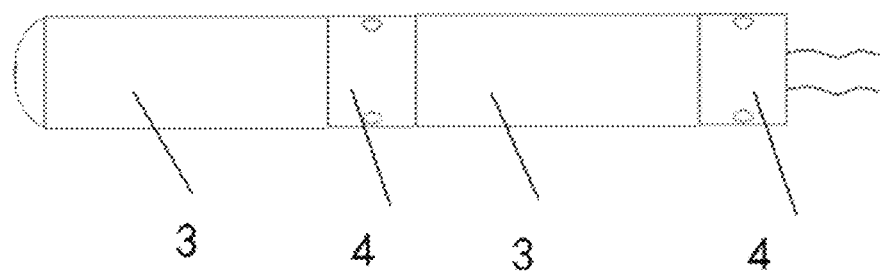
FIG. 15 is a variation diagram for the self-propelled soft robot body in embodiment 5.
Figure 15:
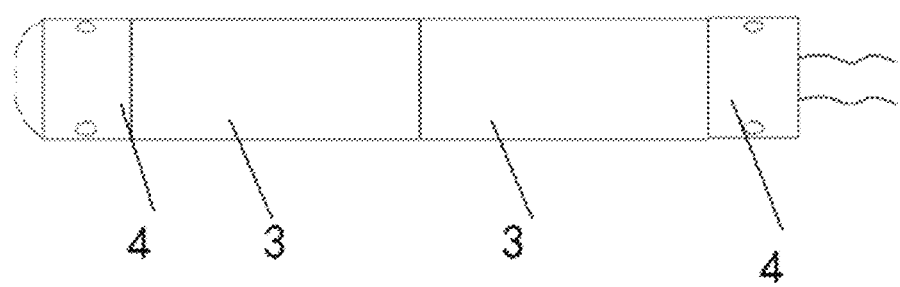

As an alternative implementation, in this embodiment, the propelling structure 3 and the support structure 4 may also adopt the combination of "propelling structure 3+support structure 4+propelling structure 3+support structure 4" or "support structure 4+propelling structure 3+propelling structure 3+support structure 4" as shown in FIG. 15.

Obviously, the above embodiments are merely intended to clearly illustrate rather than limit the numerated implementations. For one with ordinary skill in the art, other different forms of modifications or changes may further be made on the basis of the aforementioned descriptions. It is unnecessary and impossible to exhaust all implementations. And modifications or changes derived herefrom obviously fall into the protection scope of the present disclosure.

What is claimed is:

1. A self-propelled soft robot body, adapted for automatically moving in a tract, comprising a tube which is internally and axially provided with
a tube cavity,
at least one propelling structure, comprising a first driving unit, a second driving unit and a third driving unit, which are embedded within a peripheral wall of the tube cavity, relative to an axis thereof, and along the axis of the tube; and
at least two support structures, with each two adjacent support structures having the at least one propelling structure arranged therebetween;
wherein,
the first driving unit, the second driving unit and the third driving unit are respectively telescopic along the axis of the tube; and
the support structures are fixedly connected with the propelling structure and arranged about the peripheral wall of the tube cavity, for fixing at least one end of the self-propelled soft robot body on the tract, and providing support for the self-propelled soft robot body in the tract during movement.

2. The self-propelled soft robot body in accordance with claim 1, wherein,
the first driving unit, the second driving unit and the third driving unit are respectively internally provided with a first fluid accommodation cavity suitable for accommodating a fluid; and
the first fluid accommodation cavity is communicated with a fluid supply-drainage device through a first fluid supply-drainage pipe, and under an action of the fluid supply-drainage device, able to extend when pressurized or contract when depressurized along the axis.

3. The self-propelled soft robot body in accordance with claim 2, the first fluid accommodation cavity is formed in the peripheral wall of the tube, with one end connected with the first fluid supply-drainage pipe.

4. The self-propelled soft robot body in accordance with claim 2, wherein, the propelling structure further comprises a first restraint layer, which circumferentially surrounds an exterior of the tube, for restricting the extension or contraction of the first driving unit, the second driving unit and the third driving unit along the axis of the tube.

5. The self-propelled soft robot body in accordance with claim 2, wherein, the support structure comprises:
a positioning and expansion unit, fixedly arranged on the peripheral wall of the tube, adapted for expanding or contracting in an radial direction of the tube, and able to be fixed to the tract when expanding, and separated from the tract when contracting; and
a second restraint layer, surrounding the exterior of the positioning and expansion unit along an circumference of the tube, for restricting the expansion or contraction of the positioning and expansion unit in an radial direction of the tube.

6. The self-propelled soft robot body in accordance with claim 2, further comprising an outer cover which covers exteriors of the propelling structure and the support structure, and the outer cover is made of flexible material.

7. The self-propelled soft robot body in accordance with claim 2, further comprising a detection device which further comprises:
a pressure sensor, circumferentially and evenly arranged on an outer side of the support structure, adapted for detecting a pressure imposed on the tract by the support structure; and
a tension sensor, circumferentially and evenly arranged on an outer side of the propelling structure, adapted for detecting a protraction or contraction state of the propelling structure.

8. The self-propelled soft robot body in accordance with claim 1, wherein, the propelling structure further comprises a first restraint layer, which circumferentially surrounds an exterior of the tube, for restricting the extension or contraction of the first driving unit, the second driving unit and the third driving unit along the axis of the tube.

9. The self-propelled soft robot body in accordance with claim 1, wherein, the support structure comprises:
a positioning and expansion unit, fixedly arranged on the peripheral wall of the tube, adapted for expanding or contracting in n radial direction of the tube, and able to be fixed to the tract when expanding, and separated from the tract when contracting; and
a second restraint layer, surrounding the exterior of the positioning and expansion unit along an circumference of the tube, for restricting the expansion or contraction of the positioning and expansion unit in an radial direction of the tube.

10. The self-propelled soft robot body in accordance with claim 9, wherein, the positioning and expansion unit is provided with a second fluid accommodation cavity which is suitable for accommodating a fluid and is communicated with the fluid supply-drainage device through a second fluid supply-drainage pipe; the second fluid accommodation cavity is annular.

11. The self-propelled soft robot body in accordance with claim 9, wherein, the support structure further comprises a negative-pressure positioning device which is arranged on the tube and adapted for enabling the self-propelled soft robot body to be adsorbed on the tract via negative pressure, the negative-pressure positioning device comprises:
negative-pressure holes, evenly arranged on the peripheral wall of the tube and communicated with the tract; and
a negative pressure conduit, connecting the negative-pressure holes with the fluid supply-drainage device, so as to connect negative-pressured branches.

12. The self-propelled soft robot body in accordance with claim 1, further comprising an outer cover which covers exteriors of the propelling structure and the support structure, and the outer cover is made of flexible material.

13. The self-propelled soft robot body in accordance with claim 1, further comprising a detection device which further comprises:

a pressure sensor, circumferentially and evenly arranged on an outer side of the support structure, adapted for detecting a pressure imposed on the tract by the support structure; and
a tension sensor, circumferentially and evenly arranged on an outer side of the propelling structure, adapted for detecting a protraction or contraction state of the propelling structure.

* * * * *